(12) United States Patent
Hagihara et al.

(10) Patent No.: US 10,000,503 B2
(45) Date of Patent: Jun. 19, 2018

(54) POWER SUPPLY SYSTEM AND CONNECTOR

(75) Inventors: Takeshi Hagihara, Osaka (JP); Ryou Okada, Osaka (JP); Yousuke Takata, Osaka (JP); Hiroya Andoh, Aichi (JP); Yuta Ochiai, Aichi (JP); Nobuyuki Nakagawa, Aichi (JP); Yukihiro Miyashita, Aichi (JP)

(73) Assignees: SUMITOMO ELECTRIC INDUSTRIES, LTD., Osaka (JP); SUMITOMO WIRING SYSTEMS, LTD., Mie (JP); AUTONETWORKS TECHNOLOGIES, LTD., Mie (JP); TOYOTA JIDOSHA KABUSHIKI KAISHA, Aichi (JP)

( * ) Notice: Subject to any disclaimer, the term of this patent is extended or adjusted under 35 U.S.C. 154(b) by 1022 days.

(21) Appl. No.: 14/343,710

(22) PCT Filed: Sep. 7, 2012

(86) PCT No.: PCT/JP2012/072948
§ 371 (c)(1),
(2), (4) Date: Apr. 11, 2014

(87) PCT Pub. No.: WO2013/035852
PCT Pub. Date: Mar. 14, 2013

(65) Prior Publication Data
US 2014/0312840 A1    Oct. 23, 2014

(30) Foreign Application Priority Data
Sep. 9, 2011    (JP) .................................. 2011-197427

(51) Int. Cl.
*H02J 7/00*    (2006.01)
*C07D 493/04*    (2006.01)
(Continued)

(52) U.S. Cl.
CPC ........ *C07D 493/04* (2013.01); *B60L 11/1811* (2013.01); *C08G 18/3218* (2013.01);
(Continued)

(58) Field of Classification Search
USPC ......................................................... 320/109
See application file for complete search history.

(56) References Cited

U.S. PATENT DOCUMENTS 8,093,745 B2 * 1/2012 Cern ..................... G01R 15/14
307/104
2002/0171535 A1    11/2002 Cern
(Continued)

FOREIGN PATENT DOCUMENTS

| CN | 102077480 A | 5/2011 |
| JP | 61-136327 A | 6/1986 |

(Continued)

OTHER PUBLICATIONS

Japanese Office Action issued in Japanese Application No. 2013-532679 dated Oct. 6, 2015, with English translation.
(Continued)

*Primary Examiner* — Eric Lee
(74) *Attorney, Agent, or Firm* — McDermott Will & Emery LLP (57) ABSTRACT

A power supply system and a connector, which can suppress occurrence of crosstalk between a power supply wire, and a control wire and an earth wire in a charging cable that includes the power supply wire, the control wire and the earth wire at the time of connecting a power supplying device with a vehicle having a power storage device to be supplied with power from the power supplying device via the power supply wire and the earth wire to be used for supplying power and the control wire for transmitting a control signal to be used for power supply control of the
(Continued)

power storage device, are provided. The ratio of the winding number of a primary coil connected with at least one of the control wire and the earth wire to the winding number of a secondary coil connected with a communication unit that sends and receives a communication signal is set at 1/N (N>1) in a system which satisfies VnC>VnL or is set at N (N>1) in a system which satisfies VnC<VnL.

10 Claims, 5 Drawing Sheets

(51) Int. Cl.
  *H04B 3/54* (2006.01)
  *B60L 11/18* (2006.01)
  *C08G 18/32* (2006.01)
  *C08G 18/77* (2006.01)

(52) U.S. Cl.
  CPC ........... *C08G 18/771* (2013.01); *H04B 3/548* (2013.01); *H04B 2203/5425* (2013.01)

(56) References Cited

U.S. PATENT DOCUMENTS

| | | | |
|---|---|---|---|
| 2003/0076221 | A1 | 4/2003 | Akiyama et al. |
| 2003/0095036 | A1 | 5/2003 | Wasaki et al. |
| 2011/0069782 | A1 | 3/2011 | Wilson et al. |
| 2012/0002714 | A1 | 1/2012 | Varadarajan et al. |
| 2012/0029728 | A1* | 2/2012 | Hirayama ........... B60L 11/1838 701/1 |

FOREIGN PATENT DOCUMENTS

| | | |
|---|---|---|
| JP | H06225034 A | 8/1994 |
| JP | 2003-60533 | 2/2003 |
| JP | 2003060533 A | 2/2003 |
| JP | 2004-532562 A | 10/2004 |
| JP | 2007-194292 A | 8/2007 |
| JP | 2007311894 A | 11/2007 |
| JP | 2010010782 A | 1/2010 |
| JP | 2010-239850 A | 10/2010 |
| JP | 2011-015530 A | 1/2011 |

OTHER PUBLICATIONS

Chinese Office Action dated Nov. 4, 2014, issued in counterpart Chinese Patent Application No. 201280043746.X; 27 pages.
"Surface Vehicle Recommended Practice", J1772 Jan. 2010, Society of Automotive Engineers, Inc., Oct. 1996 (revised in Jan. 2010).
Peter Van den Bossche, et al., Trends and development Status of IEC Global Electric Vehicle Standards, Journal of Asian electric Vehicles, Dec. 2010, vol. 8, No. 2, pp. 1409-1414, [retrieval date Oct. 11, 2012], Internet <URL:http://www.elec.eng.osaka-cu.ac.jp/~aevc/1409-1414.pdf>.
Jim Francfort, Electric Vehicle Charging Levels and Requirements Overview, Presentation Material, Dec. 15, 2010, pp. 1-29, [retrieval date Oct. 11, 2012], Internet <URL:http://www.oregonsae.org/Meetings/EV_CHARGE_REQ_dec-15-2010.pdf>.
Cyriacus Bleijs, Low-cost charging systems with full communication capability, EVS24 International Battery, Hybrid and Fuel Cell Electric Vehicle Symposium, May 13, 2009, EVS24-Stavanger, Norway, pp. 1-9, [retrieval date Oct. 11, 2012], Internet <URL:http://www.cars21. com/assets/link/EVS-24-4660443EDF.pdf>.
SAE Electric Vehicle Conductive Charge Coupler, SAE Recommended Practice, Aug. 2001, SAE J1772, REV. Month01, pp. 1-30, [retrieval date Oct. 11, 2012] <URL:https://www.google.com/url?q=http://www.arb.ca.gov/msprog/zevprog/stakeholders/infrastructure/finalsaej1772.doc&sa-U&ei=hIR2UPv_JaaNmQXX4oHYDg&ved=0CAcQFjAA&client=internal-uds-cse&usg=AFQjCNHaJ9U1LJKdZIkhFQrIRrgWIUnasA>.
International Search Report PCT/JP2012/072948 dated Oct. 23, 2012 with English translation.
Cyriacus Bleijs, Low-cost charging systems with full communication capability, EVS24 International Battery, Hybrid and Fuel Cell Electric Vehicle Symposium, May 13, 2009, EVS24-Stavanger, Norway, pp. 1-9, [retrieval date Oct. 11, 2012], Internet <URL:http://www.cars21.com/assets/link/EVS-24-4660443EDF.pdf>.
"Surface Vehicle Information Report", J2931/4 JUL2012, Society of Automotive Engineers, Inc., Jul. 2012.
Panasonic Electronic Devices Co., Ltd., Noise Suppression Technology—How to suppress Noise—[retrieval date Feb. 3, 2014] <URL:http://industrial.panasonic.com/ww/i_e/00000/noise_e/noise_e/technical/TT0001_e.pdf>.

* cited by examiner

FIG. 3B $$VnC = 2\pi f \cdot Cs \cdot Rl \cdot Vi$$

FIG. 4A

FIG. 4B $$VnL = 2\pi f \cdot Lm \cdot RI \cdot In$$

FIG. 5

POWER SUPPLY SYSTEM AND CONNECTOR

This application is the national phase under 35 U.S.C. § 371 of PCT International Application No. PCT/JP2012/072948 which has an International filing date of Sep. 7, 2012 and designated the United States of America.

FIELD

The present invention relates to: a power supply system in which a power supplying device connects with a vehicle, which has a power storage device be supplied with power from the power supplying device, via a power supply wire and an earth wire to be used for supplying power and a control wire for transmitting a control signal to be used for power supply control of the power storage device; and a connector to be used in the power supply system.

BACKGROUND

In recent years, an electric vehicle and a hybrid electric vehicle, which have devices such as a motor and a battery and run by driving the motor with power stored in the battery, have begun to spread. In an electric vehicle, an outside power supplying device needs to supply power to the battery, and even some of hybrid electric vehicles are plug-in hybrid electric vehicles in which an outside power supplying device may supply power to the battery. In a vehicle wherein supplying power from outside to the battery is performed, a plug of a charging cable, which includes a power supply wire connected with an outside power supplying device, is connected with a connector device of a power supplying port provided in the vehicle. In addition, power supply from the power supplying device to the battery of the vehicle is performed via the charging cable.

Moreover, the power supplying device is connected with the vehicle via a control wire for sending and receiving a control pilot signal at the time of supplying power from the power supplying device to the battery of the vehicle, and charge control based on the control pilot signal is performed at the time of charging. Moreover, a communication system for superimposing another communication signal on communication, in which a control wire is used, has been proposed (see "SURFACE VEHICLE RECOMMENDED PRACTICE", J1772 JAN2010, Society of Automotive Engineers, Inc., October 1996 (revised in January 2010), for example).

SUMMARY

However, at the time of implementation of a communication system described in "SURFACE VEHICLE RECOMMENDED PRACTICE", J1772 JAN2010, Society of Automotive Engineers, Inc., October 1996 (revised in January 2010), a charging cable necessary for supplying power includes a power supply wire, an earth wire and a control wire. In addition, the length of the charging cable sometimes reaches 10 m. Therefore, when superimposition of a communication signal of 2 to 30 MHz with a voltage of several Vpp is performed in regard to the control wire, there is a problem that a communication signal superimposed on a control pilot signal causes crosstalk at the power supply wire. It is needless to say that such crosstalk has a bad influence on phenomena such as supplying power, and there is a problem that shipment of a product is sometimes restricted when criteria pertaining to a compliance test necessary for a regulation for attachment of a FCC mark, a VCCI mark, a CE mark, or the like is not met.

An example of a method for suppressing crosstalk is a method for suppressing the power level of a communication signal superimposed at a control wire. Here, when the power level of a communication signal is suppressed, an influence of noise caused by various electronic equipment mounted on a vehicle becomes relatively large, and therefore the S/N ratio (signal-to-noise ratio) deteriorates, which leads to a problem that the communication performance degrades.

The present invention has been made in view of such a situation, and the object thereof is to provide a power supply system and a connector which can suppress occurrence of crosstalk by suppressing the voltage level or the current level of a communication signal without excess suppression of the output level of power of a communication signal.

In a power supply system according to the present invention, a power supplying device connects with a vehicle, which has a power storage device to be supplied with power from the power supplying device, via a power supply wire and an earth wire to be used for supplying power and a control wire for transmitting a control signal to be used for power supply control of the power storage device. The vehicle comprises: a communication unit that sends and receives a communication signal, which is different from the control signal; and a vehicle side superimposition/separation unit that performs superimposition/separation of the communication signal in regard to the control wire and the earth wire. The vehicle side superimposition/separation unit comprises a signal converter of an electromagnetic induction type having a primary coil, which is connected with at least one of the control wire and the earth wire, and a secondary coil, which is coupled electromagnetically with the primary coil and is connected with the communication unit. A ratio of winding number of the primary coil to winding number of the secondary coil is M/N (N>M). The power supplying device comprises a power supplying device side superimposition/separation unit that performs superimposition/separation of the communication signal for communication via the control wire and the earth wire.

In the power supply system according to the present invention, a system related to communication of the communication signal has a characteristic that an influence of crosstalk due to a capacitive reactance component between the control wire and the earth wire, and the power supply wire is larger than an influence of crosstalk due to an inductive reactance component between the control wire and the earth wire, and the power supply wire.

In a power supply system according to the present invention, a power supply device connects with a vehicle, which has a power storage device to be supplied with power from the power supplying device, via a power supply wire and an earth wire to be used for supplying power and a control wire for transmitting a control signal to be used for power supply control of the power storage device. The vehicle comprises: a communication unit that sends and receives a communication signal, which is different from the control signal; and a vehicle side superimposition/separation unit that performs superimposition/separation of the communication signal in regard to the control wire and the earth wire. The vehicle side superimposition/separation unit comprises a signal converter of an electromagnetic induction type having a primary coil, which is connected with at least one of the control wire and the earth wire, and a secondary coil, which is coupled electromagnetically with the primary coil and is connected with the communication unit. A ratio of winding number of the primary coil to winding number of the secondary coil is N/M (N>M). The power supplying device comprises a power supplying device side superimposition/separation unit that performs superimposition/separation of the communication signal for communication via the control wire and the earth wire.

In the power supply system according to the present invention, a system related to communication of the communication signal has a characteristic that an influence of crosstalk due to a capacitive reactance component between the control wire and the earth wire, and the power supply wire is smaller than an influence of crosstalk due to an inductive reactance component between the control wire and the earth wire, and the power supply wire.

In the power supply system according to the present invention, the power supplying device further comprises a power supplying device side communication unit that sends and receives the communication signal. The power supplying device side superimposition/separation unit comprises a signal converter of an electromagnetic induction type having a primary coil, which is connected with at least one of the control wire and the earth wire, and a secondary coil, which is coupled electromagnetically with the primary coil and is connected with the power supplying device side communication unit. A ratio of winding number of the primary coil to winding number of the secondary coil provided in the power supplying device side superimposition/separation unit is substantially equal to a ratio of winding number of the primary coil to winding number of the secondary coil provided in the vehicle side superimposition/separation unit.

In the power supply system according to the present invention, the primary coil is interposed in the control wire or the earth wire, or in both.

In the power supply system according to the present invention, the primary coil is connected with two branch lines which branch respectively from the control wire and the earth wire.

A connector according to the present invention comprises: connecting means for connecting a power supply wire and an earth wire necessary for supplying power to a power storage device mounted on a vehicle and a control wire for transmitting a control signal to be used for power supply control of the power storage device with a vehicle exterior cable; and a superimposition/separation unit that performs superimposition/separation of a communication signal, which is different from the control signal, in regard to the control wire and the earth wire. The superimposition/separation unit comprises a signal convertor of an electromagnetic induction type having a primary coil, which is connected with at least one of the control wire and the earth wire, and a secondary coil, which is coupled electromagnetically with the primary coil and is connected with a communication unit that sends and receives the communication signal. A ratio of winding number of the primary coil to winding number of the secondary coil is M/N (N>M).

A connector according to the present invention comprises: connecting means for connecting a power supply wire and an earth wire necessary for supplying power to a power storage device mounted on a vehicle and a control wire for transmitting a control signal to be used for power supply control of the power storage device with a vehicle exterior cable; and a superimposition/separation unit that performs superimposition/separation of a communication signal, which is different from the control signal, in regard to the control wire and the earth wire. The superimposition/separation unit comprises a signal convertor of an electromagnetic induction type having a primary coil, which is connected with at least one of the control wire and the earth wire, and a secondary coil, which is coupled electromagnetically with the primary coil and is connected with a communication unit that sends and receives the communication signal. A ratio of winding number of the primary coil to winding number of the secondary coil is N/M (N>M).

In the present invention, it is possible to suppress the voltage level or the current level of a communication signal according to the characteristics of a system related to communication without excess suppression of the power level of a communication signal, by designing properly the ratio of the winding number of a primary coil to the winding number of a secondary coil.

A power supply system and a connector according to the present invention can suppress the voltage level or the current level of a communication signal according to the characteristics of a system related to communication, by designing properly the ratio of the winding number of a primary coil to the winding number of a secondary coil. Accordingly, the present invention has a superior effect of, for example, making it possible to suppress occurrence of crosstalk without deteriorating the S/N ratio. In addition, the present invention has a superior effect of, for example, making it possible to suppress a bad influence on phenomena such as supplying power by suppressing occurrence of crosstalk and to produce an excellent product which meets criteria pertaining to a variety of compliance tests related to product shipment or the like.

The above and further objects and features will move fully be apparent from the following detailed description with accompanying drawings.

DETAILED DESCRIPTION OF NON-LIMITING EXAMPLE EMBODIMENTS

The following description will explain the present invention in detail with reference to the drawings for illustrating some embodiments thereof.

Embodiment 1

Figure 1:
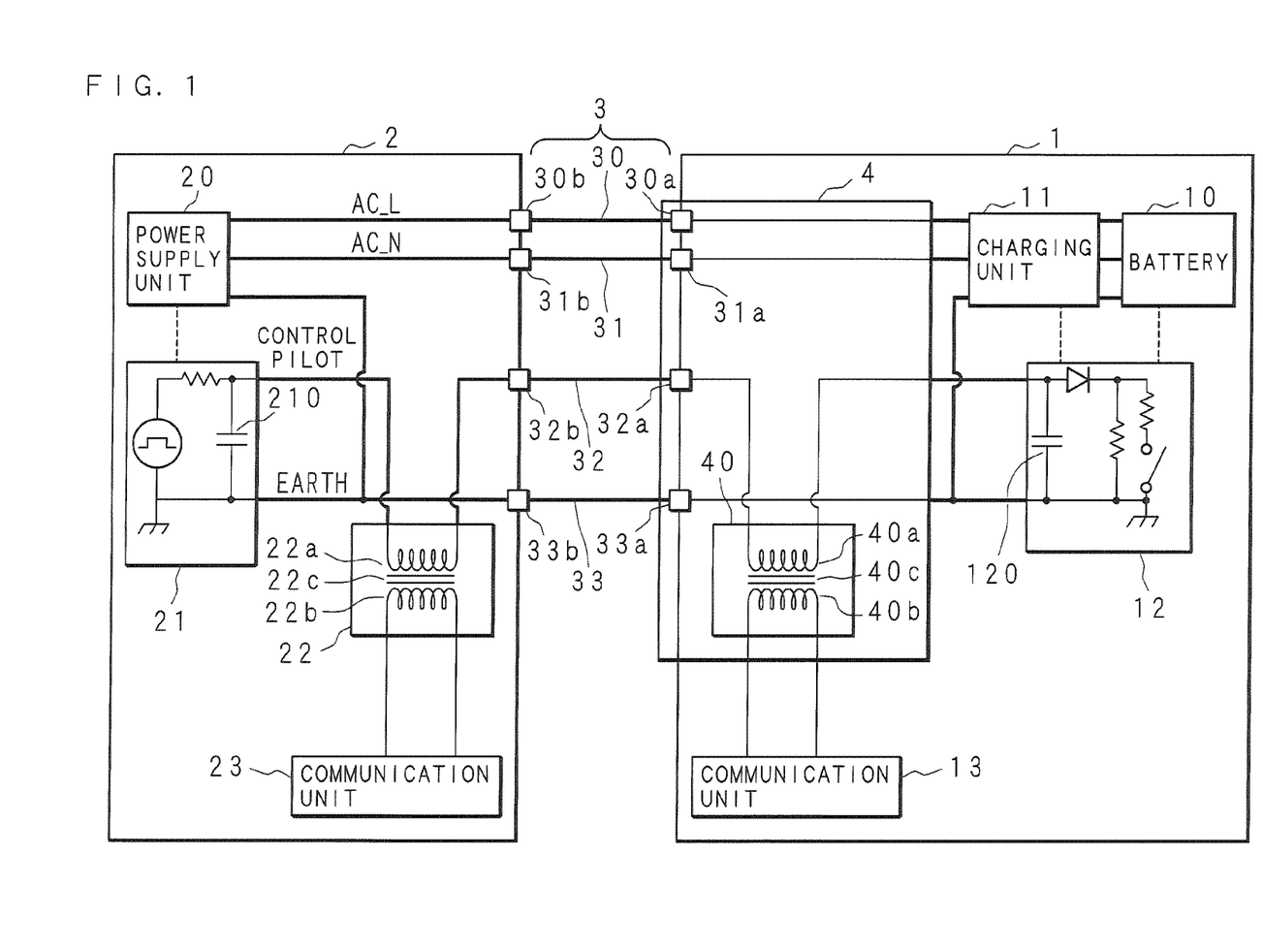
FIG. 1 is an explanatory drawing for illustrating a configuration example of a power supply system according to Embodiment 1 of the present invention.

FIG. 1 is an explanatory drawing for illustrating a configuration example of a power supply system according to Embodiment 1 of the present invention. FIG. 1 illustrates an example wherein a power supply system of the present invention is applied to power supply control at the time of supplying power from a power supplying device 2 such as a charging station to a battery (power storage device) 10 provided in a vehicle 1 such as an electric vehicle or a plug-in hybrid electric vehicle.

The vehicle 1 and the power supplying device 2 can be connected with each other via a charging cable 3. The charging cable 3 includes two power supply wires 30 and 31 to be used as electricity supply wires, a control wire 32 for transmitting a control signal such as a control pilot signal to be used for charge control, and an earth wire 33 which is a lead for earthing. One end of the charging cable 3 is connected at the power supplying device 2 side, and a plug provided at the other end side can be connected with a connector 4 disposed as a junction at the vehicle 1 side. By connecting the other end of the charging cable 3 with the connector 4, the power supply wires 30 and 31, the control wire 32 and the earth wire 33 in the charging cable 3 are coupled with connection terminals 30a, 31a, 32a and 33a provided in the connector 4, so that a circuit configuration illustrated in FIG. 1 is obtained.

The power supply wires 30 and 31 are AC wires to which alternating-current voltage is applied. The control wire 32 is a signal wire for sending and receiving a control signal such as a control pilot signal, and charge control is performed on the basis of a control pilot signal to be sent and received. Furthermore, in the power supply system according to the present invention, information to be used for management such as charging management or accounting management, or a variety of other information is transmitted as a communication signal, which is different from a control signal, using two leads of the control wire 32 and the earth wire 33. That is, a power supply system of the present invention is constructed to superimpose a communication signal on a control signal (control pilot signal) for communication via two cables of the control wire 32 and the earth wire 33 and to establish communication.

The power supplying device 2 is provided with an power supply unit 20 that supplies alternating-current power, a charge control unit 21 that establishes communication pertaining to charge control, a superimposition/separation unit 22 that performs superimposition and separation of a communication signal, and a communication unit 23 that sends and receives a communication signal.

The power supply unit 20 is connected with one ends of the power supply wires 30 and 31, and with the earth wire 33. The charge control unit 21 is connected with one end of the control wire 32 and with the earth wire 33. It is to be noted that the power supply wires 30 and 31 and the earth wire 33 are connected from the power supply unit 20 to another device or wiring. The power supply wires 30 and 31, the control wire 32 and the earth wire 33 in the following description include an extension line part disposed as an inside lead for convenience, although wiring in the power supplying device 2 is an inside lead which functions as an extension line connected with the power supply wires 30 and 31, the control wire 32 and the earth wire 33 included in the charging cable 3 outside the power supplying device 2 via connection terminals 30b, 31b, 32b and 33b.

The charge control unit 21 is a circuit at an output side compliant with International Standard related to charge control, for example, and performs charge control in various states such as connection confirm or initiation of energization by sending and receiving a control signal such as a control pilot signal. In the charge control unit 21, a capacitor 210 for connecting the control wire 32 with the earth wire 33, a variety of elements and circuits such as an oscillation circuit that oscillates a control signal, and other various circuits, which are not illustrated in the figure, such as a microcomputer and a buffer to be used for detecting the state of the power supply unit 20 and the battery 10 and for deciding a control signal to be oscillated are disposed.

The superimposition/separation unit 22 is disposed on the control wire 32 at a position between the charge control unit 21 and the connection terminal 32b. The superimposition/separation unit 22 is provided with a primary coil 22a, a secondary coil 22b and a magnetic core 22c, which compose a coupling transformer (signal converter of electromagnetic induction type), and the primary coil 22a of the coupling transformer is provided to be interposed in the control wire 32. The secondary coil 22b of the coupling transformer is connected with the communication unit 23. Although a state where the primary coil 22a is interposed in the control wire 32 is illustrated here, it is to be noted that the present invention is not limited to this, and the primary coil 22a may be interposed in the earth wire 33, or in both of the control wire 32 and the earth wire 33.

The superimposition/separation unit 22 superimposes a variety of communication signals on communication of a control signal such as a control pilot signal via the control wire 32 and separates a variety of superimposed communication signals. Communication by the communication unit 23 is established when the superimposition/separation unit 22 superimposes a variety of communication signals outputted from the communication unit 23 and inputs a variety of separated communication signals into the communication unit 23.

In addition to the battery 10 and the connector 4, the vehicle 1 is provided with a charging unit 11 that charges the battery 10, a charge control unit 12 that establishes communication pertaining to charge control, and a communication unit 13 that sends and receives a communication signal.

The vehicle 1 is connected with the other end of the charging cable 3, and therefore the other ends of the power supply wires 30 and 31, the other end of the control wire 32, and the other end of the earth wire 33 included in the charging cable 3 are connected with inside wiring of the vehicle 1. The other ends of the power supply wires 30 and 31 are connected with the charging unit 11 via an AC wire disposed inside the vehicle 1, and the charging unit 11 charges the battery 10. The other end of the control wire 32 is connected with the charge control unit 12 via an extension line disposed as inside wiring in the vehicle 1. In addition, the other end of the earth wire 33 is connected with the charging unit 11 and the battery 10, and with the charge control unit 12 via an extension line disposed as inside wiring in the vehicle 1. It is to be noted that a tip of the AC wire connected with the power supply wires 30 and 31, a tip of an extension line connected with the control wire 32, and a tip of an extension line connected with the earth wire 33 are inserted in an insertion hole provided in the connector 4. By connecting the connector 4 with the charging cable 3, the power supply wires 30 and 31, the control wire 32 and the earth wire 33 in the charging cable 3 are connected with wiring inside the connector 4. It is to be noted that the power supply wires 30 and 31, the control wire 32 and the earth wire 33 in the following description also include the AC wire and the inside wiring for convenience.

The charge control unit 12 is a circuit at an input side compliant with International Standard related to charge control, for example, and performs charge control in various states such as connection confirm or initiation of energization by sending and receiving a control signal such as a control pilot signal. In the charge control unit 12, a variety of elements such as a capacitor 120 for connecting the control wire 32 with the earth wire 33, and various other circuits, which are not illustrated in the figure, such as a microcomputer and a buffer to be used for processing based on a control signal and for detection of the state of the battery 10 and the charging unit 11 are disposed. It is to be noted that the circuit configuration illustrated in FIG. 1 is only an example and can be designed properly by, for example, providing the capacitor 120 in the connector 4.

The connector 4 is provided with a superimposition/separation unit 40 that performs superimposition/separation of a communication signal, and the control wire 32 is inserted in the superimposition/separation unit 40. Moreover, the superimposition/separation unit 40 is provided with a primary coil 40a interposed in the control wire 32, a secondary coil 40b connected with the communication unit 13, and a magnetic core 40c as a coupling transformer (signal converter of electromagnetic induction type). The magnetic core 40c has an annular or baculiform shape and is wound by the primary coil 40a and the secondary coil 40b. In addition, the superimposition/separation unit 40 superimposes a communication signal on communication of a control signal via the control wire 32 and separates a superimposed communication signal. Although a state where the primary coil 40a is interposed in the control wire 32 is illustrated here, it is to be noted that the present invention is not limited to this, and the primary coil 40a may be interposed in the earth wire 33, or in both of the control wire 32 and the earth wire 33. Communication by the communication unit 13 is established when the superimposition/separation unit 40 in the connector 4 superimposes a variety of communication signals to be outputted from the communication unit 13 and inputs a variety of separated communication signals into the communication unit 13 as described above. That is, at the time of transmission of a control signal, it becomes possible to realize communication for superimposing and separating a communication signal, and to send and receive information to be used for management such as charge amount management or accounting management as a communication signal.

By connecting the power supplying device 2 with the vehicle 1 via the power supply wires 30 and 31, the control wire 32 and the earth wire 33 included in the charging cable 3, an energizing path, which is constituted of the power supply wires 30 and 31, and a transmission path, which is constituted of the control wire 32, of a control signal are secured, and earthing is achieved. In a state where the power supplying device 2 is connected with the vehicle 1 via the control wire 32 and the earth wire 33, a current loop circuit is constructed which is closed by the control wire 32, the earth wire 33, the capacitor 210, the primary coil 22a of the power supplying device 2, the primary coil 40a in the connector 4, and the capacitor 120. In addition, the superimposition/separation unit 22 in the power supplying device 2 and the superimposition/separation unit 40 in the connector 4, which are disposed as a coupling transformer in the loop, can superimpose and separate a communication signal, and communication can be established between the power supplying device 2 and the vehicle 1.

Figure 2:
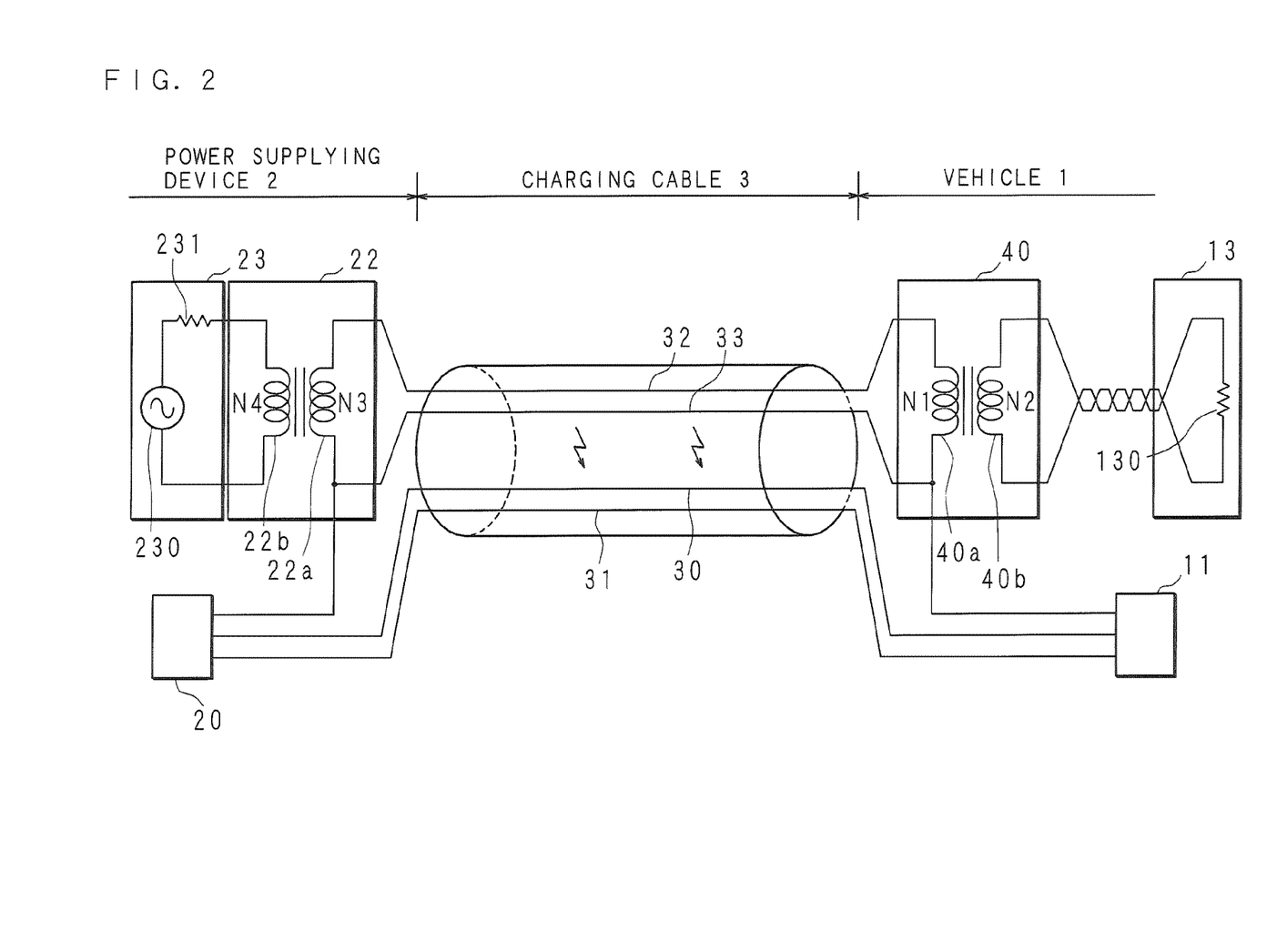
FIG. 2 is a schematic diagram for illustrating a configuration example of the power supply system according to Embodiment 1 of the present invention.

FIG. 2 is a schematic diagram for illustrating a configuration example of the power supply system according to Embodiment 1 of the present invention. FIG. 2 relates to communication for performing superimposition/separation of a communication signal in regard to the control wire 32 and the earth wire 33 in the power supply system illustrated in FIG. 1 and further illustrates a configuration example of a case where the power supplying device 2 transmits a communication signal and the vehicle 1 receives the communication signal.

The communication unit 23 that performs a sending process at the power supplying device 2 side can be illustrated as an equivalent circuit in which a transmitter 230 for transmitting a communication signal and a resistance 231 are used as illustrated in FIG. 2. Moreover, the communication unit 13 that performs a receiving process at the vehicle 1 side can be illustrated as an equivalent circuit in which a resistance 130 is used as illustrated in FIG. 2.

Moreover, the winding numbers of the primary coil 40a and the secondary coil 40b provided in the superimposition/separation unit 40 at the vehicle 1 side are respectively N1 and N2, and the winding numbers of the primary coil 22a and the secondary coil 22b provided in the superimposition/separation unit 22 at the power supplying device 2 side are respectively N3 and N4.

As illustrated in FIG. 2, the power supply wires 30 and 31 are adjacent to the control wire 32 and the earth wire 33 where a communication signal is superimposed, since the power supply wires 30 and 31, the control wire 32 and the earth wire 33 are included in the charging cable 3. Therefore, transmission of a signal such as a communication signal using the control wire 32 and the earth wire 33 as a medium may possibly have an influence on the power supply wires 30 and 31 as crosstalk.

Figure 3A:
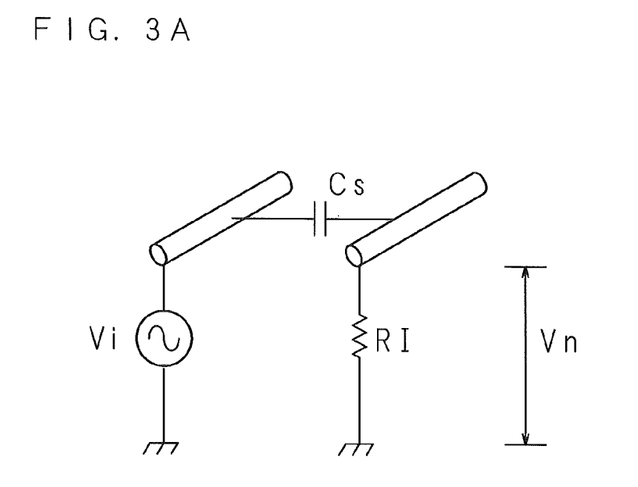
FIG. 3A is an explanatory drawing for illustrating an example of crosstalk due to electrostatic coupling.
Figure 3B:
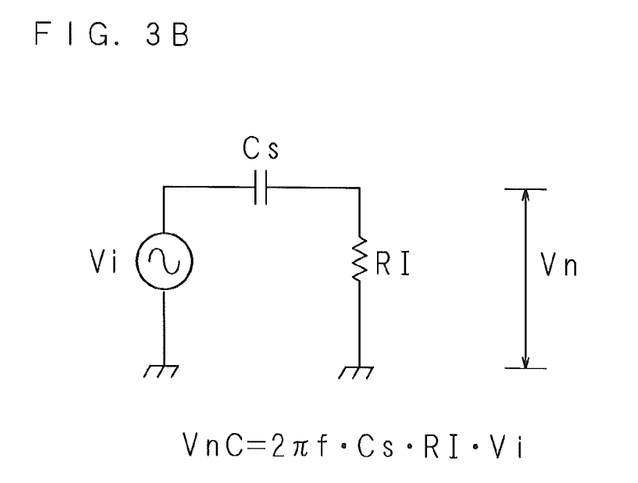
FIG. 3B is an explanatory drawing for illustrating an example of crosstalk due to electrostatic coupling.

FIGS. 3A and 3B are explanatory drawings for illustrating an example of crosstalk due to electrostatic coupling. FIG. 3A illustrates schematically crosstalk due to electrostatic coupling which occurs between two communication wires, and FIG. 3B illustrates an equivalent circuit of FIG. 3A. When two communication wires for transmitting a signal are adjacent to each other, the communication wires can be considered to be connected at a capacitor, capacitive reactance of which is Cs. Furthermore, assuming that the frequency of a signal to be transmitted is f, the signal source voltage is Vi and the load impedance between the communication wire and the earthing potential is RI, the crosstalk voltage VnC due to electrostatic coupling can be represented as the following Expression 1.

$$VnC = 2\pi f \cdot Cs \cdot RI \cdot Vi \quad \text{(Expression 1)}$$

Crosstalk occurs on the power supply wires 30 and 31 due to transmission of a signal such as a communication signal, a medium of which is the control wire 32 and the earth wire 33. Therefore the power supply system of the present invention is more complicated than a model illustrated in FIGS. 3A and 3B. However, the power system of the present invention can be considered to be substantially same as the model illustrated in FIGS. 3A and 3B. Accordingly, it is also possible to represent the crosstalk voltage VnC due to electrostatic coupling as the following Expression 2 in the power supply system according to Embodiment 1 of the present invention illustrated in FIG. 2.

$$VnC = 2\pi f \cdot Cs \cdot RI \cdot Vi \quad \text{(Expression 2)}$$

Here,
  f: a frequency of a communication signal to be transmitted from the transmitter 230
  Cs: an capacitive reactance between the control wire 32 and the earth wire 33, and the power supply wires 30 and 31
  RI: a load impedance at the near end side between the control wire 32 and the earth wire 33, and the power supply wires 30 and 31
  Vi: a signal source voltage of a communication signal to be transmitted from the transmitter 230

Figure 4A:
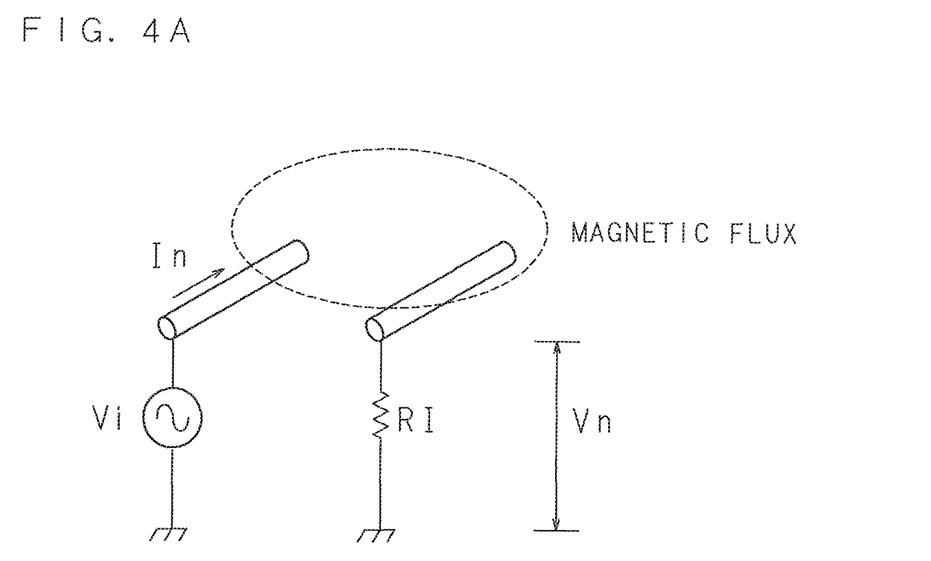
FIG. 4A is an explanatory drawing for illustrating an example of crosstalk due to electromagnetic coupling.
Figure 4B:
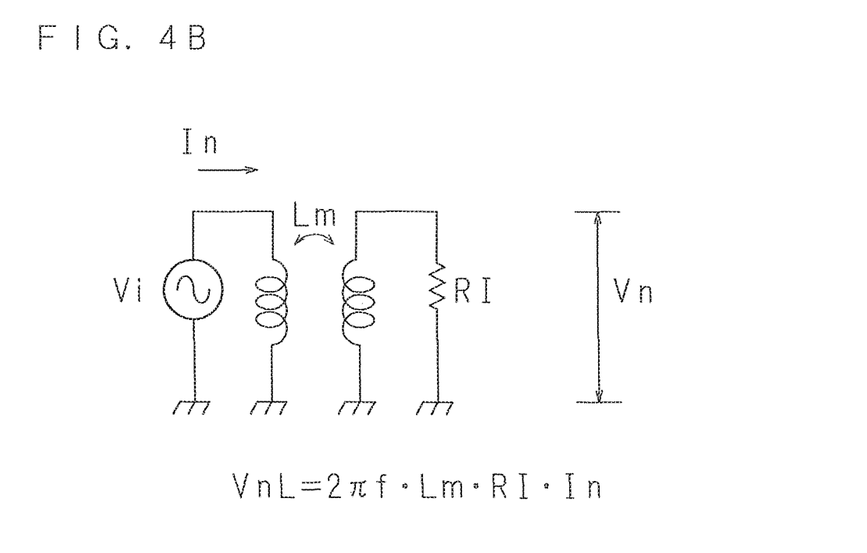
FIG. 4B is an explanatory drawing for illustrating an example of crosstalk due to electromagnetic coupling.

FIGS. 4A and 4B are explanatory drawings for illustrating an example of crosstalk due to electromagnetic coupling.

FIG. 4A illustrates schematically crosstalk due to electromagnetic coupling which occurs between two communication wires, and FIG. 4B illustrates an equivalent circuit of FIG. 4A. When two communication wires for transmitting a signal are adjacent to each other, the communication wires can be considered to have a coil, an inductive reactance of which is Lm. Furthermore, assuming that the frequency of a signal to be transmitted is f, the signal source current is In and the load impedance between the communication wire and the earthing potential is RI, the crosstalk voltage VnL due to electromagnetic coupling can be represented as the following Expression 3.

$$VnL = 2\pi f \cdot Lm \cdot RI \cdot In \qquad \text{(Expression 3)}$$

Crosstalk occurs on the power supply wires 30 and 31 due to transmission of a signal such as a communication signal, a medium of which is the control wire 32 and the earth wire 33. Therefore the power supply system of the present invention is more complicated than a model illustrated in FIGS. 4A and 4B. However, the power system of the present invention can be consider to be substantially same as the model illustrated in FIGS. 4A and 4B. Accordingly, it is also possible to represent the crosstalk voltage VnL due to electromagnetic coupling as the following Expression 4 in the power supply system according to Embodiment 1 of the present invention illustrated in FIG. 2.

$$VnL = 2\pi f \cdot Lm \cdot RI \cdot In \qquad \text{(Expression 4)}$$

Here, f: a frequency of a communication signal to be transmitted from the transmitter 230

Lm: an inductive reactance between the control wire 32 and the earth wire 33, and the power supply wires 30 and 31

RI: a load impedance at the near end side between the control wire 32 and the earth wire 33, and the power supply wires 30 and 31

In: a signal source current of a communication signal to be transmitted from the transmitter 230

In an actual power supply system, both of crosstalk due to electrostatic coupling and crosstalk due to electromagnetic coupling may possibly occur. It is to be noted that a crosstalk voltage Vn, which is the total of the crosstalk voltage VnC due to electrostatic coupling and the crosstalk voltage VnL due to electromagnetic coupling, can be measured using an LISN (Line Impedance Stabilization Network). The LISN is a device for performing processing such as acquisition of data of conductive emission in implementation of a test related to criteria for a CE mark or the like and has functions such as measurement of the crosstalk voltage Vn.

In the power supply system of the present invention, the ratio of the winding number of the primary coil 40a to the winding number of the secondary coil 40b at the vehicle 1 side (N1/N2) and the ratio of the winding number of the primary coil 22a to the winding number of the secondary coil 22b at the power supplying device 2 side (N3/N4) are designed according to the characteristics of a system related to communication which can be represented as a correlation between the crosstalk voltage VnC due to electrostatic coupling and the crosstalk voltage VnL due to electromagnetic coupling.

Specifically, when VnC>VnL is satisfied, N1:N2 and N3:N4 are designed in such a manner that the winding number N2 of the secondary coil 40b becomes larger than the winding number N1 of the primary coil 40a, and the winding number N4 of the secondary coil 22b becomes larger than the winding number N3 of the primary coil 22a. That is, when VnC>VnL is satisfied, N1:N2 (N3:N4) is designed in such a manner that the ratio of the winding number of the primary coil 40a (22a) to the winding number of the secondary coil 40b (22b) becomes 1/N (N>1). Although the representation 1/N (N>1) is used here, it is to be noted that the representation can be generalized as M/N (N>M), since it is only required that the winding number at the primary coil 40a (22a) side is smaller than the winding number at the secondary coil 40b (22b) side.

When the winding number ratio becomes 1/N (N>1), this causes step-down of the signal voltage level in the charging cable 3, and therefore it is possible to suppress crosstalk in a system having a high crosstalk voltage VnC due to electrostatic coupling. For example, when the winding number ratio is 1/10 and the signal source voltage Vi is 5 Vpp, it becomes possible to suppress the signal voltage on the charging cable 3 to 500 mVpp. Since it is possible to suppress the sending voltage against the sending power as described above, it becomes possible to suppress crosstalk without deteriorating the S/N ratio (signal-to-noise ratio).

Although it is preferable that the winding number ratio at the vehicle 1 side is substantially equal to the winding number ratio at the power supplying device 2 side in order to maintain favorable communication quality, it is to be noted that the ratio of the winding number of the primary coil 22a to the winding number of the secondary coil 22b at the power supplying device 2 side (N3/N4) may be one.

When VnC<VnL is satisfied, similar effects can be obtained by reversing the winding number ratio. Specifically, when VnC<VnL is satisfied, N1:N2 and N3:N4 are designed in such a manner that the winding number N2 of the secondary coil 40b becomes smaller than the winding number N1 of the primary coil 40a, and the winding number N4 of the secondary coil 22b becomes smaller than the winding number N3 of the primary coil 22a. That is, when VnC<VnL is satisfied, N1:N2 (N3:N4) is designed in such a manner that the ratio of the winding number of the primary coil 40a (22a) to the winding number of the secondary coil 40b (22b) becomes N (N>1). Although the representation N (N>1) is used here, it is to be noted that the representation can be generalized as N/M (N>M), since it is only required that the winding number at the primary coil 40a (22a) side is larger than the winding number at the secondary coil 40b (22b) side.

When the winding number ratio becomes N (N>1), this causes step-up of the signal voltage level in the charging cable 3, and therefore it is possible to suppress crosstalk in a system having a high crosstalk voltage VnL due to electromagnetic coupling. Since it is possible to suppress the sending current against the sending power as described above, it becomes possible to suppress crosstalk without deteriorating the S/N ratio (signal-to-noise ratio).

Although it is also preferable that the winding number ratio at the vehicle 1 side is substantially equal to the winding number ratio at the power supplying device 2 side in such a case in order to maintain favorable communication quality, it is to be noted that the ratio of the winding number of the primary coil 22a to the winding number of the secondary coil 22b at the power supplying device 2 side (N3/N4) may be one.

When VnC=VnL is satisfied, N1:N2 and N3:N4 are designed in such a manner that the winding number N1 of the primary coil 40a becomes equal to the winding number N2 of the secondary coil 40b, and the winding number N3 of the primary coil 22a becomes equal to the winding number N4 of the secondary coil 22b. That is, when VnC=VnL is satisfied, N1:N2 (N3:N4) is designed in such a manner that the ratio of the winding number of the primary coil 40a (22a) to the winding number of the secondary coil 40b (22b) becomes one.

A power supply system according to Embodiment 1 of the present invention can be realized in such a manner.

Embodiment 2

Embodiment 2 is a mode wherein the primary coil of the superimposition/separation unit is not interposed in the control wire nor the earth wire in Embodiment 1, and a branch unit and a branch line are provided at the control wire and the earth wire, and the primary coil of the superimposition/separation unit is connected with the branch line. It is to be noted that reference numerals similar to those of Embodiment 1 are used to refer to configurations similar to those of Embodiment 1 in the following description so that Embodiment 1 can be referred, and explanation thereof will be omitted.

Figure 5:
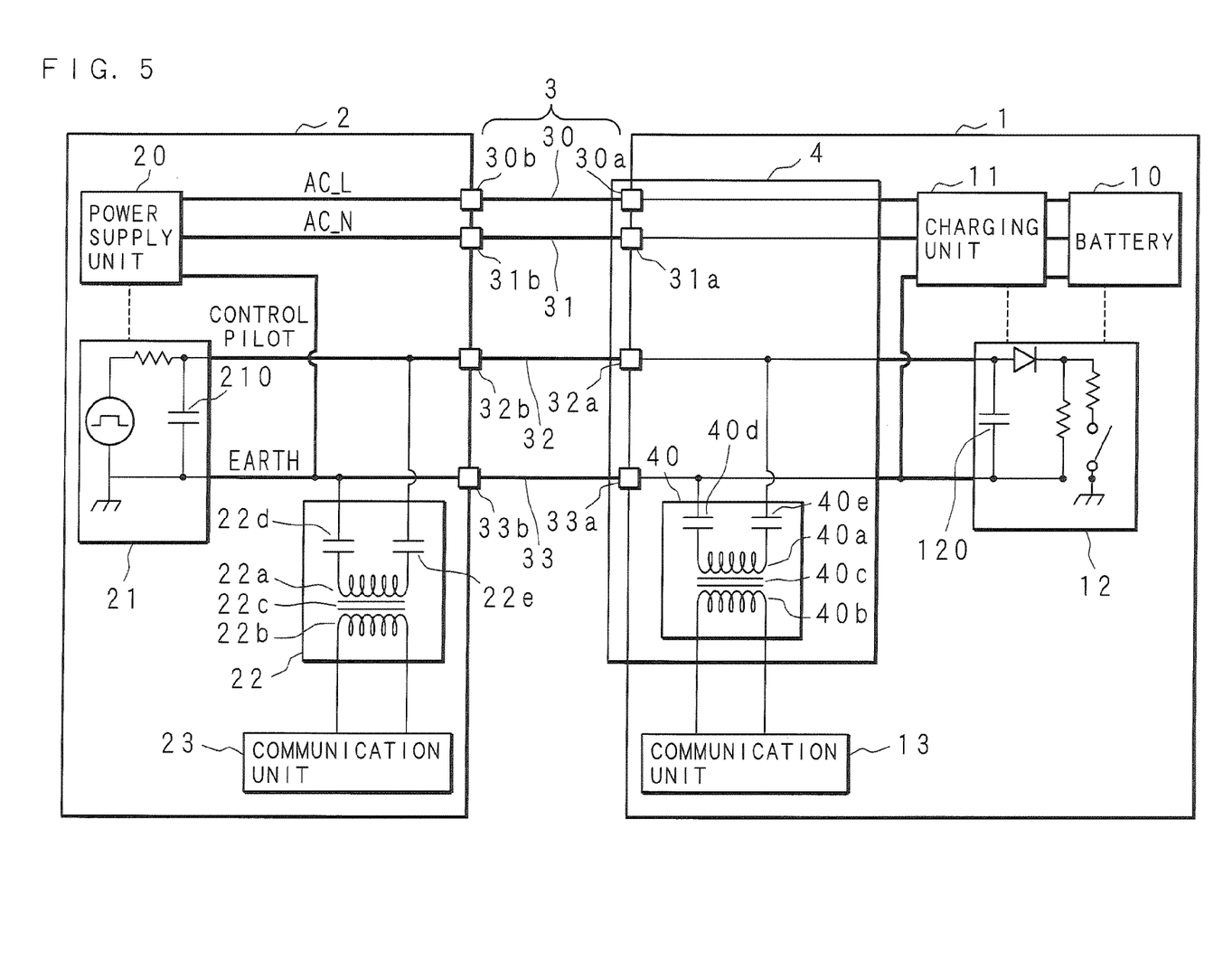
FIG. 5 is an explanatory drawing for illustrating a configuration example of a power supply system according to Embodiment 2 of the present invention.

FIG. 5 is an explanatory drawing for illustrating a configuration example of the power supply system according to Embodiment 2 of the present invention. A charge control unit 21 provided in a power supplying device 2 is connected with one ends of a control wire 32 and an earth wire 33. The other ends of the control wire 32 and the earth wire 33 are connected to a charging cable 3 via connection terminals 32b and 33b.

The control wire 32 and the earth wire 33 are connected respectively with one ends of branch lines which branch at positions between the charge control unit 21 and the connection terminals 32b and 33b, and the other ends of two branch lines are connected with a superimposition/separation unit 22. In the superimposition/separation unit 22, the other ends of the two branch lines are connected with terminals at one end sides of condensers 22d and 22e. Terminals at the other end sides of the condensers 22d and 22e are connected with a primary coil 22a included in the coupling transformer. In addition, a secondary coil 22b of the coupling transformer is connected with a communication unit 23.

The superimposition/separation unit 22 superimposes a variety of communication signals on communication of a control signal via a branch line and separates a variety of superimposed communication signals. Communication by the communication unit 23 is established when the superimposition/separation unit 22 superimposes a variety of communication signals to be outputted from the communication unit 23 and inputs a variety of separated communication signals into the communication unit 23.

The control wire 32 and the earth wire 33 are inserted in a connector 4 provided in a vehicle 1. The control wire 32 and the earth wire 33 are connected respectively with one ends of branch lines which branch in the connector 4, and the other ends of two branch lines are connected with a superimposition/separation unit 40. In the superimposition/separation unit 40, the other ends of the two branch lines are connected with terminals at one end sides of the condensers 40d and 40e. Terminals at the other end sides of the condensers 40d and 40e are connected with a primary coil 40a included in the coupling transformer. In addition, a secondary coil 40b of the coupling transformer is connected with a communication unit 13.

The superimposition/separation unit 40 superimposes a variety of communication signals on communication of a control signal via a branch line and separates a variety of superimposed communication signals. Communication by the communication unit 13 is established when the superimposition/separation unit 40 superimposes a communication signal to be outputted from the communication unit 13 and inputs a variety of separated communication signals into the communication unit 13. That is, at the time of transmission of a control signal, it becomes possible to realize communication for superimposing and separating a communication signal, and to send and receive information to be used for management such as charge amount management or accounting management as a communication signal.

By connecting the power supplying device 2 with the vehicle 1 via power supply wires 30 and 31, the control wire 32 and the earth wire 33 included in the charging cable 3, an energizing path, which is constituted of the power supply wires 30 and 31, and a transmittance path, which is constituted of the control wire 32, of a control signal are secured and earthing is achieved. In a state where the power supplying device 2 is connected with the vehicle 1 via the control wire 32 and the earth wire 33, a current loop circuit is constructed which is closed by the control wire 32, the earth wire 33, two branch lines in the superimposition/separation unit 22 of the power supplying device 2, the condensers 22d and 22e and the primary coil 22a, and two branch lines in the superimposition/separation unit 40 of the connector 4, the condensers 40d and 40e, and the primary coil 40a. In addition, the superimposition/separation unit 22 in the power supplying device 2 and the superimposition/separation unit 40 in the connector 4, which are disposed as a coupling transformer in the loop, can superimpose and separate a communication signal and establish communication between the power supplying device 2 and the vehicle 1.

A correlation between a system related to communication and the ratio of the winding number of the primary coil 40a (22a) to the winding number of the secondary coil 40b (22b) in Embodiment 2 is similar to that of Embodiment 1.

Specifically, when VnC>VnL is satisfied, N1:N2 and N3:N4 are designed in such a manner that the winding number N2 of the secondary coil 40b becomes larger than the winding number N1 of the primary coil 40a, and the winding number N4 of the secondary coil 22b becomes larger than the winding number N3 of the primary coil 22a. That is, when VnC>VnL is satisfied, N1:N2 (N3:N4) is designed in such a manner that the ratio of the winding number of the primary coil 40a (22a) to the winding number of the secondary coil 40b (22b) becomes 1/N (N>1). Although the representation 1/N (N>1) is used here, it is to be noted that the representation can be generalized as M/N (N>M), since it is only required that the winding number at the primary coil 40a (22a) side is smaller than the winding number at the secondary coil 40b (22b) side.

When VnC<VnL is satisfied, similar effects can be obtained by reversing the winding number ratio. Specifically, when VnC<VnL is satisfied, N1:N2 and N3:N4 are designed in such a manner that the winding number N2 of the secondary coil 40b becomes smaller than the winding number N1 of the primary coil 40a, and the winding number N4 of the secondary coil 22b becomes smaller than the winding number N3 of the primary coil 22a. That is, when VnC<VnL is satisfied, N1:N2 (N3:N4) is designed in such a manner that the ratio of the winding number of the primary coil 40a (22a) to the winding number of the secondary coil 40b (22b) becomes N (N>1). Although the representation N (N>1) is used here, it is to be noted that the representation can be generalized as N/M (N>M), since it is only required that the winding number at the primary coil 40a (22a) side is larger than the winding number at the secondary coil 40b (22b) side.

When VnC=VnL is satisfied, N1:N2 and N3:N4 are designed in such a manner that the winding number N1 of the primary coil 40a becomes equal to the winding number N2 of the secondary coil 40b, and the winding number N3 of the primary coil 22a becomes equal to the winding number N4 of the secondary coil 22b. That is, when VnC=VnL is satisfied, N1:N2 (N3:N4) is designed in such a manner that the ratio of the winding number of the primary coil 40a (22a) to the winding number of the secondary coil 40b (22b) becomes one.

Embodiments 1 and 2 disclose only a part of innumerable examples of the present invention, and it is possible to develop the embodiments to various modes by setting the winding number ratio for voltage step-up or voltage step-down according to the characteristics related to a system of communication.

It is possible to develop the embodiments to various modes by, for example, providing superimposition/separation unit of a vehicle outside the connector.

Moreover, it is unnecessary to fix the winding number ratio, and it is possible to develop the embodiments to various modes by, for example, making the winding number ratio variable, so that the winding number ratio can be set properly according to the characteristics of a communication cable.

Although the control wire 32 is used for transmitting a control signal to be used for charge control and the control wire 32 and the earth wire 33 are used for transmitting a communication signal in the above description, a conductor such as the body of the vehicle 1 or a housing of the power supplying device 2 may be used for one or both of transmission of a control signal to be used for charge control and transmission of a communication signal.

The invention claimed is:

1. A power supply system in which a power supplying device connects with a vehicle, which has a power storage device to be supplied with power from the power supplying device, via a power supply wire and an earth wire to be used for supplying power and a control wire for transmitting a control signal to be used for power supply control of the power storage device,
wherein the vehicle comprises:
a communication unit that sends and receives a communication signal, which is different from the control signal; and
a vehicle side superimposition/separation unit that performs superimposition/separation of the communication signal in regard to the control wire and the earth wire,
wherein the vehicle side superimposition/separation unit comprises a signal converter of an electromagnetic induction type having a primary coil, which is connected with at least one of the control wire and the earth wire, and a secondary coil, which is coupled electromagnetically with the primary coil and is connected with the communication unit,
wherein a ratio of winding number of the primary coil to winding number of the secondary coil is less than one to achieve communication of the communication signal having a characteristic that an influence of crosstalk due to a capacitive reactance component between the control wire and the earth wire, and the power supply wire is larger than an influence of crosstalk due to an inductive reactance component between the control wire and the earth wire, and the power supply wire, and
wherein the power supplying device comprises a power supplying device side superimposition/separation unit that performs superimposition/separation of the communication signal for communication via the control wire and the earth wire.

2. The power supply system according to claim 1,
wherein the power supplying device further comprise a power supplying device side communication unit that sends and receives the communication signal,
wherein the power supplying device side superimposition/separation unit comprises a signal converter of an electromagnetic induction type having a primary coil, which is connected with at least one of the control wire and the earth wire, and a secondary coil, which is coupled electromagnetically with the primary coil and is connected with the power supplying device side communication unit,
wherein a ratio of winding number of the primary coil to winding number of the secondary coil provided in the power supplying device side superimposition/separation unit is substantially equal to a ratio of winding number of the primary coil to winding number of the secondary coil provided in the vehicle side superimposition/separation unit.

3. The power supply system according to claim 1,
wherein the primary coil is interposed in the control wire or the earth wire, or in both.

4. The power supply system according to claim 1,
wherein the primary coil is connected with two branch lines which branch respectively from the control wire and the earth wire.

5. A power supply system in which a power supplying device connects with a vehicle, which has a power storage device to be supplied with power from the power supplying device, via a power supply wire and an earth wire to be used for supplying power and a control wire for transmitting a control signal to be used for power supply control of the power storage device,
wherein the vehicle comprises:
a communication unit that sends and receives a communication signal, which is different from the control signal; and
a vehicle side superimposition/separation unit that performs superimposition/separation of the communication signal in regard to the control wire and the earth wire,
wherein the vehicle side superimposition/separation unit comprises a signal converter of an electromagnetic induction type having a primary coil, which is connected with at least one of the control wire and the earth wire, and a secondary coil, which is coupled electromagnetically with the primary coil and is connected with the communication unit,
wherein a ratio of winding number of the primary coil to winding number of the secondary coil is more than one to achieve communication of the communication signal having a characteristic that an influence of crosstalk due to a capacitive reactance component between the control wire and the earth wire, and the power supply wire is smaller than an influence of crosstalk due to an inductive reactance component between the control wire and the earth wire, and the power supply wire, and
wherein the power supplying device comprises a power supplying device side superimposition/separation unit that performs superimposition/separation of the communication signal for communication via the control wire and the earth wire.

6. The power supply system according to claim 5,
wherein the power supplying device further comprise a power supplying device side communication unit that sends and receives the communication signal,
wherein the power supplying device side superimposition/separation unit comprises a signal converter of an electromagnetic induction type having a primary coil, which is connected with at least one of the control wire and the earth wire, and a secondary coil, which is coupled electromagnetically with the primary coil and is connected with the power supplying device side communication unit,
wherein a ratio of winding number of the primary coil to winding number of the secondary coil provided in the power supplying device side superimposition/separation unit is substantially equal to a ratio of winding number of the primary coil to winding number of the secondary coil provided in the vehicle side superimposition/separation unit.

7. The power supply system according to claim 5,
wherein the primary coil is interposed in the control wire or the earth wire, or in both.

8. The power supply system according to claim 5,
wherein the primary coil is connected with two branch lines which branch respectively from the control wire and the earth wire.

9. A connector, comprising:
a connecting unit for connecting a power supply wire and an earth wire necessary for supplying power to a power storage device mounted on a vehicle and a control wire for transmitting a control signal to be used for power supply control of the power storage device with a vehicle exterior cable; and
a superimposition/separation unit that performs superimposition/separation of a communication signal, which is different from the control signal, in regard to the control wire and the earth wire,
wherein the superimposition/separation unit comprises a signal convertor of an electromagnetic induction type having a primary coil, which is connected with at least one of the control wire and the earth wire, and a secondary coil, which is coupled electromagnetically with the primary coil and is connected with a communication unit that sends and receives the communication signal, and
wherein a ratio of winding number of the primary coil to winding number of the secondary coil is less than one to achieve communication of the communication signal having a characteristic that an influence of crosstalk due to a capacitive reactance component between the control wire and the earth wire, and the power supply wire is larger than an influence of crosstalk due to an inductive reactance component between the control wire and the earth wire, and the power supply wire.

10. A connector, comprising:
a connecting unit for connecting a power supply wire and an earth wire necessary for supplying power to a power storage device mounted on a vehicle and a control wire for transmitting a control signal to be used for power supply control of the power storage device with a vehicle exterior cable; and
a superimposition/separation unit that performs superimposition/separation of a communication signal, which is different from the control signal, in regard to the control wire and the earth wire,
wherein the superimposition/separation unit comprises a signal convertor of an electromagnetic induction type having a primary coil, which is connected with at least one of the control wire and the earth wire, and a secondary coil, which is coupled electromagnetically with the primary coil and is connected with a communication unit that sends and receives the communication signal, and
wherein a ratio of winding number of the primary coil to winding number of the secondary coil is more than one to achieve communication of the communication signal having a characteristic that an influence of crosstalk due to a capacitive reactance component between the control wire and the earth wire, and the power supply wire is smaller than an influence of crosstalk due to an inductive reactance component between the control wire and the earth wire, and the power supply wire.

* * * * *